(12) United States Patent
Barrett et al.

(10) Patent No.: US 7,928,397 B2
(45) Date of Patent: Apr. 19, 2011

(54) GAMMA CAMERA INCLUDING A SCINTILLATOR AND AN IMAGE INTENSIFIER

(75) Inventors: Harrison H. Barrett, Tucson, AZ (US); Lars R. Furenlid, Tucson, AZ (US); H. Bradford Barber, Tucson, AZ (US); Brian W. Miller, Tucson, AZ (US)

(73) Assignee: The Arizona Board of Regents on Behalf of the University of Arizona, Tucson, AZ (US)

( * ) Notice: Subject to any disclaimer, the term of this patent is extended or adjusted under 35 U.S.C. 154(b) by 0 days.

(21) Appl. No.: 12/197,120

(22) Filed: Aug. 22, 2008

(65) Prior Publication Data

US 2009/0050811 A1  Feb. 26, 2009

Related U.S. Application Data

(60) Provisional application No. 60/965,910, filed on Aug. 23, 2007.

(51) Int. Cl.
G01T 1/20 (2006.01)
A61B 6/00 (2006.01)
G01N 23/00 (2006.01)
G21K 7/00 (2006.01)

(52) U.S. Cl. ........ 250/361 R; 378/4; 600/407; 250/362; 250/370.09; 250/370.11

(58) Field of Classification Search .............. 250/361 R, 250/363.04, 370.11, 362, 370.09; 378/4; 600/407
See application file for complete search history.

(56) References Cited

U.S. PATENT DOCUMENTS

| | | | | |
|---|---|---|---|---|
| 3,758,780 A | * | 9/1973 | Lee | 250/271 |
| 5,245,191 A | * | 9/1993 | Barber et al. | 250/363.04 |
| 5,308,986 A | * | 5/1994 | Walker | 250/370.11 |
| 5,671,264 A | * | 9/1997 | Florent et al. | 378/98 |
| 5,825,033 A | * | 10/1998 | Barrett et al. | 250/370.1 |
| 6,281,509 B1 | * | 8/2001 | Ryan et al. | 250/397 |
| 6,631,284 B2 | * | 10/2003 | Nutt et al. | 600/427 |
| 2006/0081770 A1 | * | 4/2006 | Buchin | 250/214 VT |

OTHER PUBLICATIONS

Gagnon, D., Pouliot, N., Laperriere, L., Therrien, M., and P. Oliver (1996). "Maximum Likelihood Positioning in the Scintillation Camera Using Depth of Interaction." IEEE Trans. Med. Imag. (12) 1: 101-7.*
G.A. De Vree, A. H.Westra, I. Moody, F. Van Der Have, K. M. Ligtvoet, and F. J. Beekman (2005). "Photon-Counting Gamma Camera Based on an Electron-Multiplying CCD". IEEE Trans. Nucl. Sci. (52) 3: 580-8.*
Miller et al. (2006). "Single-Photon Spatial and Energy Resolution Enhancement of a Columnar CsI(TI) / EMCCD Gamma-Camera Using Maximum-Likelihood Estimation." SPIE 6142: 6142T1-10.*
Tipnis et al. (2003). "High-Speed X-ray Imaging Camera for Time-Resolved Diffraction Studies." IEEE Trans. Nucl. Sci. (49) 5: p. 2415-2419.*

* cited by examiner

*Primary Examiner* — David P Porta
*Assistant Examiner* — Casey Bryant
(74) *Attorney, Agent, or Firm* — Oblon, Spivak, McClelland, Maier & Neustadt, L.L.P.

(57) ABSTRACT

A gamma-ray or X-ray detection device including a scintillator configured to convert gamma rays or X-rays into optical radiation, an optical image intensifier configured to intensify the optical radiation to generate intensified optical radiation, an optical coupling system configured to guide the intensified optical radiation, and a solid state detector configured to detect the intensified optical radiation to generate an interaction image representing a gamma-ray or X-ray energy emission.

18 Claims, 14 Drawing Sheets

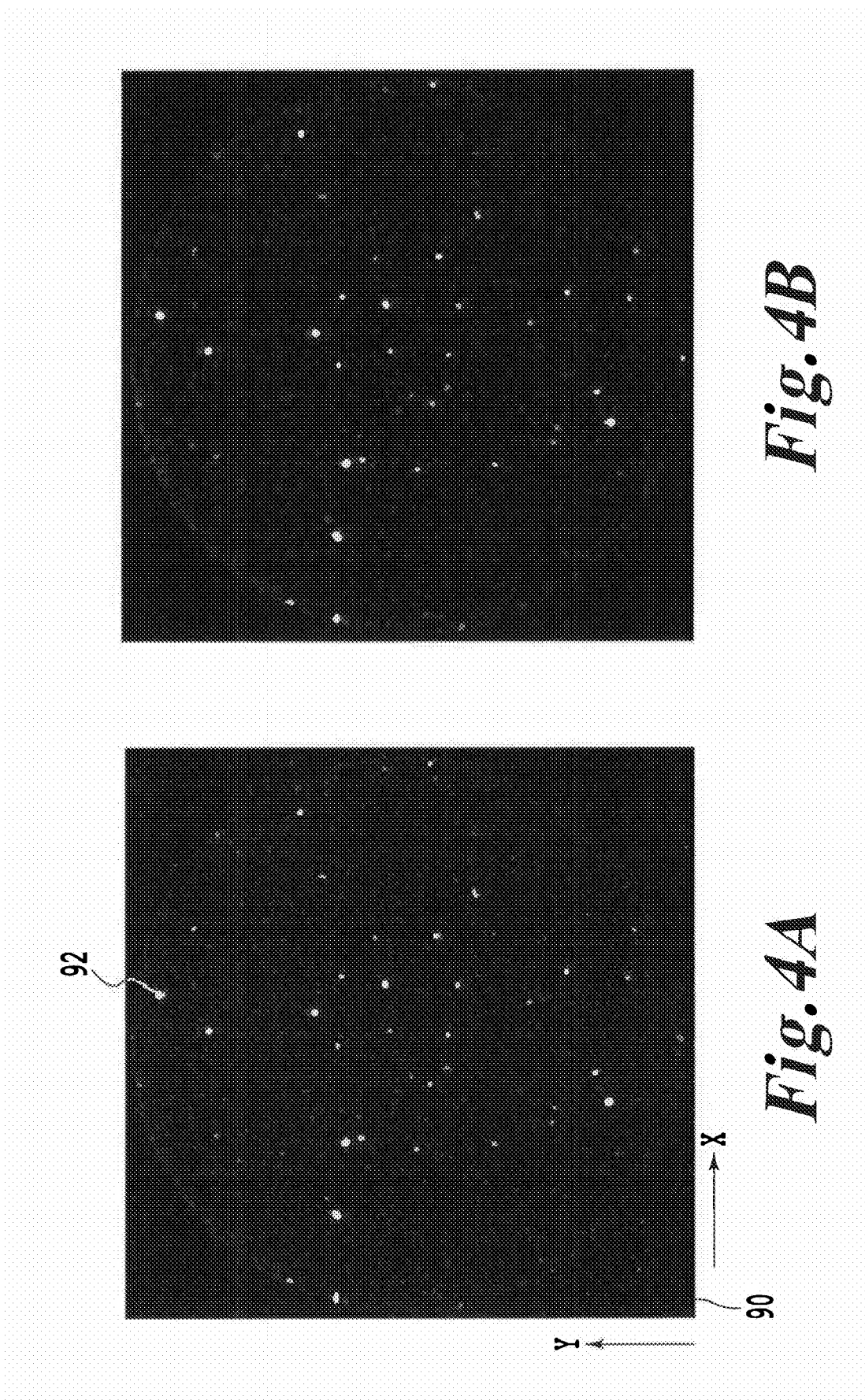

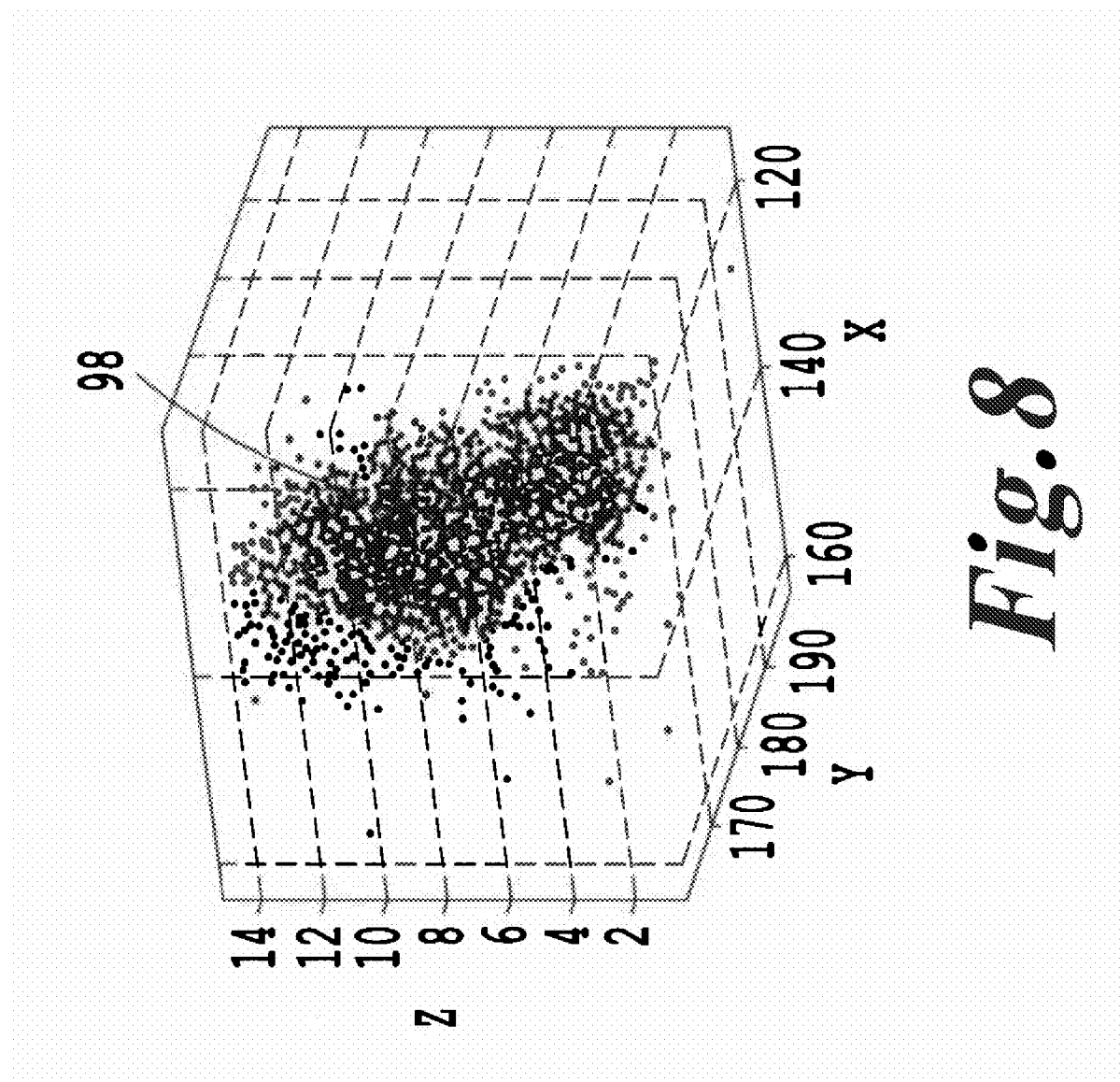

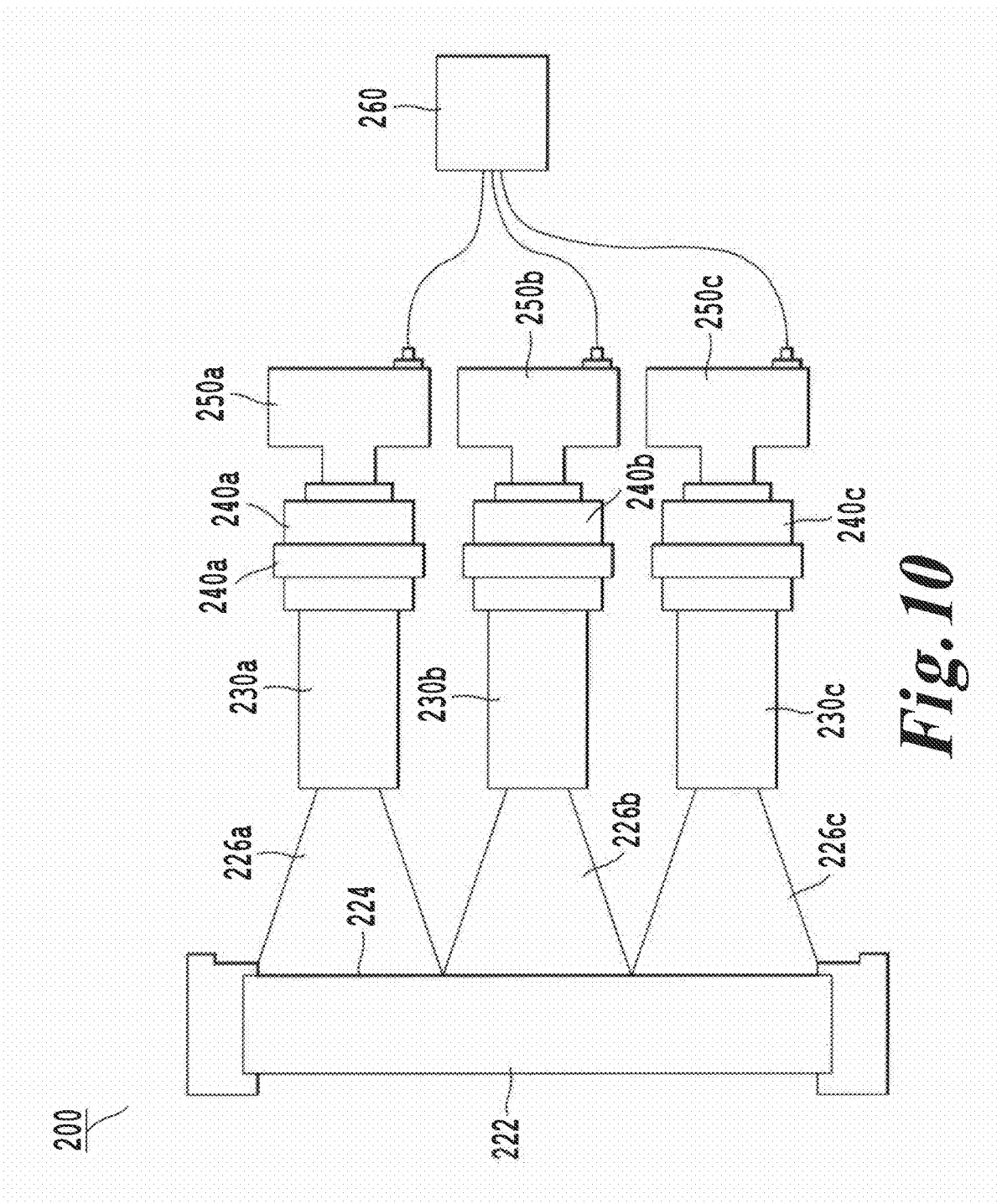

GAMMA CAMERA INCLUDING A SCINTILLATOR AND AN IMAGE INTENSIFIER

CROSS REFERENCE TO RELATED PATENT DOCUMENTS

The present patent application claims priority to the provisional Application with the Ser. No. 60/965,910 that was filed on Aug. 23, 2007 all the contents thereof being herewith incorporated by reference.

BACKGROUND OF THE INVENTION (a) Field of the Invention

The present invention relates to a high-resolution, modular gamma or X-ray camera based on a scintillator and an image intensifier having a strong optical gain that are optically coupled to a solid state detector.

(b) Brief Description of the Related Art

In the field of single photon emission computed tomography (SPECT) and molecular imaging, gamma-ray detectors with high spatial resolution are used. Currently, the high-resolution requirement for such systems can be satisfied by using a gamma-ray detector based on high-speed and low-noise charge coupled devices (CCD). Such detectors yield a spatial resolution that is sufficient to satisfy the high-resolution measurement requirements. In these detectors, a scintillation flash is observed as a cluster of signal spread over multiple pixels of the CCD. A few varieties of such detectors exist and each requires the use of a low-noise, high-quantum-efficiency CCD to observe the scintillation events. Such detectors typically consist of thin scintillators optically coupled to an expensive Electron-Multiplying CCD imager (EMCCD) where charge gain is applied within the CCD pixels. A fiber-optic taper that increases the field of view can be used to increase the active imaging area but at the expense of light intensity, thus making cluster detection difficult as well as imposing a limitation of the usable thickness of the scintillation crystal for gamma-ray detection.

Another system utilizes a scintillator attached to an electrostatic demagnifying tube (DM) which provides slight gain and an increase in the active imaging area, but light loss in the system requires coupling to an EMCCD via a fiber-optic taper to compensate for the losses. Another CCD-based gamma-ray detector is capable of imaging individual gamma-ray interactions using a high-efficiency optical configuration and a low-noise, high-quantum efficiency, cooled CCD imagers. Substantial disadvantages of this system are that it only works with relatively thin scintillators that are less sensitive, and the CCD used for the detection must be configured to use long readout time for reduced noise which greatly reduces the frame rate capability of the system.

Despite all of the above mentioned improvements in the field of gamma-ray detection as discussed above, there is a strong need for increased sensitivity and read-out frequency of the measured scintillations to detect gamma-ray sources for many different applications, such as small-animal SPECT and molecular imaging. Advances in systems are therefore strongly desired requiring high-resolution, high-speed, and highly-sensitive gamma-ray detectors, without substantially increasing the costs of such a system.

SUMMARY OF THE INVENTION

One aspect of the present invention provides a gamma-ray detection device. Preferably, the gamma-ray detection device includes a scintillator configured to convert the gamma-rays into optical radiation, an optical image intensifier configured to intensify the optical radiation to generate intensified optical radiation, and an optical coupling system configured to guide the intensified optical radiation. In addition, the gamma-ray detection device preferably further includes a solid state detector configured to detect the intensified optical radiation to generate an interaction image representing an energy emission of the gamma ray.

According to another aspect of the present invention, a method of estimating the horizontal position, the vertical position, the depth, and the energy of an interaction of the gamma ray in a scintillator is provided. The method preferably includes the steps of absorbing a gamma ray in a scintillator to convert gamma-ray energy into optical photons to produce an optical image on a rear surface of the scintillator, intensifying the optical image to produce an intensified image, projecting the intensified image onto an image sensor, and capturing the intensified image and converting the intensified image into a digital data image. In addition, the method preferably further includes the step of processing the digital data image by a maximum-likelihood estimation to estimate the horizontal position, the vertical position, the depth, and the energy of the interaction of the gamma-ray in the scintillator.

According to yet another aspect of the present invention, a system for capturing tomographic imaging data is provided. The system preferably includes a plurality of aperture plates arranged around an inspection area, the plates having at least one pinhole. In addition, the system preferably includes a plurality of gamma-ray detection devices that are arranged around the inspection area so that a plurality of respective optical axes of the plurality of gamma-ray detection devices intersect with the inspection area, the plurality of aperture plates arranged between the detection devices and the inspection area. In addition, in the system preferably each of the plurality of gamma-ray detection devices is arranged at a different angle of orientation towards the inspection area.

According to still another aspect of the present invention, a gamma-ray detection apparatus is provided. The detection apparatus preferably includes a scintillator configured to convert gamma rays into optical radiation, a first optical image intensifier configured to intensify optical radiation from a first portion of a rear surface of the scintillator to generate first intensified optical radiation, and a second optical image intensifier configured to intensify optical radiation from a second portion of the rear surface of the scintillator to generate second intensified optical radiation. Moreover, the apparatus preferably also includes a first and second optical coupling system configured to guide the first and second intensified optical radiation, respectively; and a first and second solid state detector configured to detect the first and second intensified optical radiation to generate a first and second interaction image, respectively, representing a gamma-ray energy emission.

The summary of the invention is neither intended nor should it be construed as being representative of the full extent and scope of the present invention, which additional aspects will become more readily apparent from the detailed description, particularly when taken together with the appended drawings.

BRIEF DESCRIPTION OF THE DRAWINGS

These and other features, aspects and advantages of the present invention will become better understood with regard to the following description, appended claims and accompanying drawings where:

FIGS. 4A, 4B, 4C, and 4D show an unprocessed and a series of processed images generated by the detector of the gamma camera representing clusters;

FIG. 8 shows a three-dimensional representation of the estimates of positions where gamma rays interacted in the scintillator;

FIG. 10 shows a diagrammatical cross-sectional view of a gamma-camera apparatus having multiple detectors coupled to a single scintillator plate for tiling.

Herein, identical reference numerals are used, where possible, to designate identical elements that are common to the figures. The images in the drawings are simplified for illustrative purposes and are not depicted to scale.

DETAILED DESCRIPTION OF THE INVENTION

Figure 1:
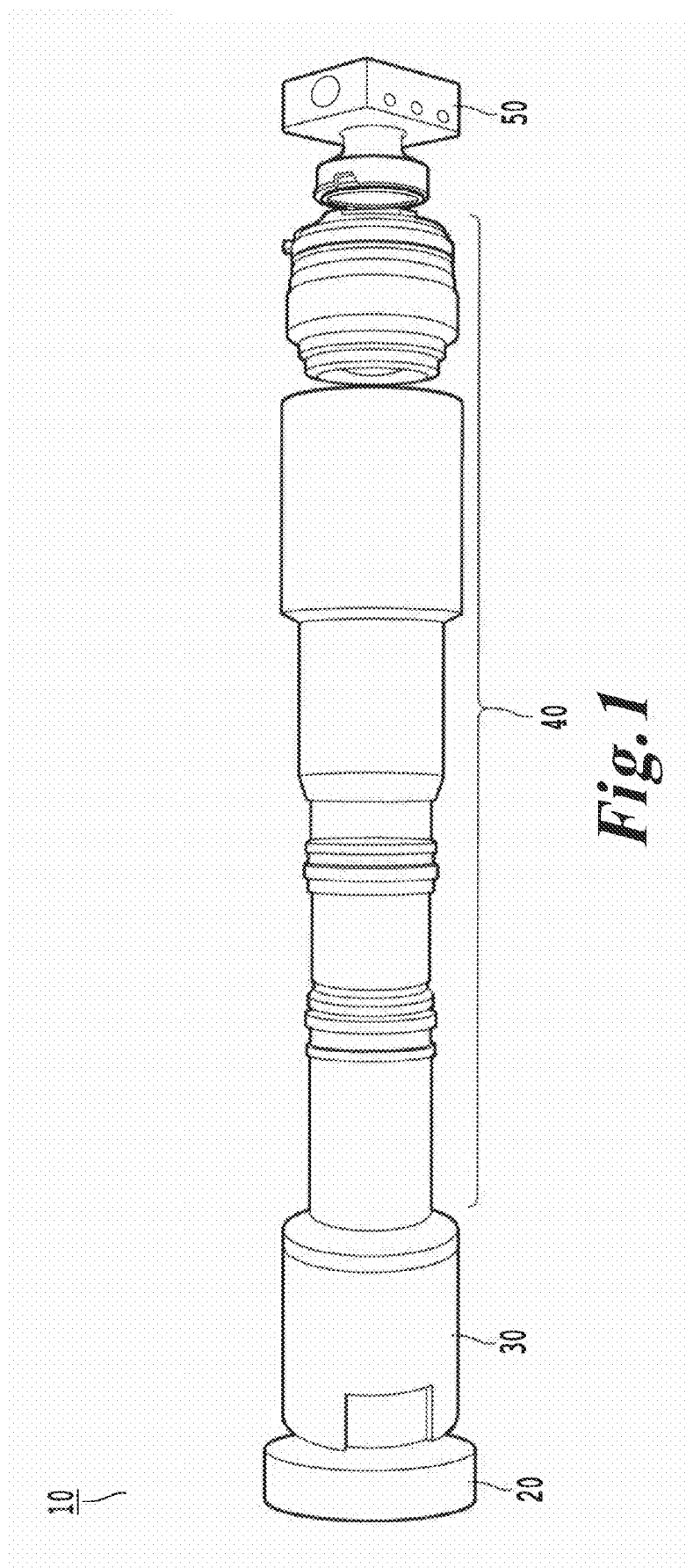
FIG. 1 shows a view of the gamma camera according to an embodiment of the present invention.

In accordance with the present invention, a gamma camera is schematically illustrated in FIG. 1, and is referred to throughout by reference numeral 10. First, a scintillator 20 is arranged that can convert the gamma rays or X rays from a corresponding source into optical radiation, such as visible light, to form a light emitting pattern or image on a rear surface of scintillator 20. Scintillator 20 is coupled to an image intensifier 30 that can amplify light emitted by scintillator 20. An interface between scintillator 20 and image intensifier 30 is arranged to minimize light loss and distortion between these two elements. After the image intensifier 30, an optical system 40 is arranged, for example an objective lens that can either magnify or minify an image formed by the amplified light. The image formed by the optical system 40 is then focused on an image sensor of a detector 50 that is connected to the optical system 40. The detector 50 is configured to read out a measurement image that measures the light emitting pattern produced by the scintillator, and further data and image processing can be performed on the measurement image. Gamma camera 10 can be used for various applications, such as molecular imaging with radiotracers, for example small-animal SPECT imaging. A gamma-ray microscope can be designed based on the gamma camera 10. In addition, the present invention is also useful for non-tomographic imaging of isotopes. It can provide a very high resolution compared to conventional systems.

Figure 2:
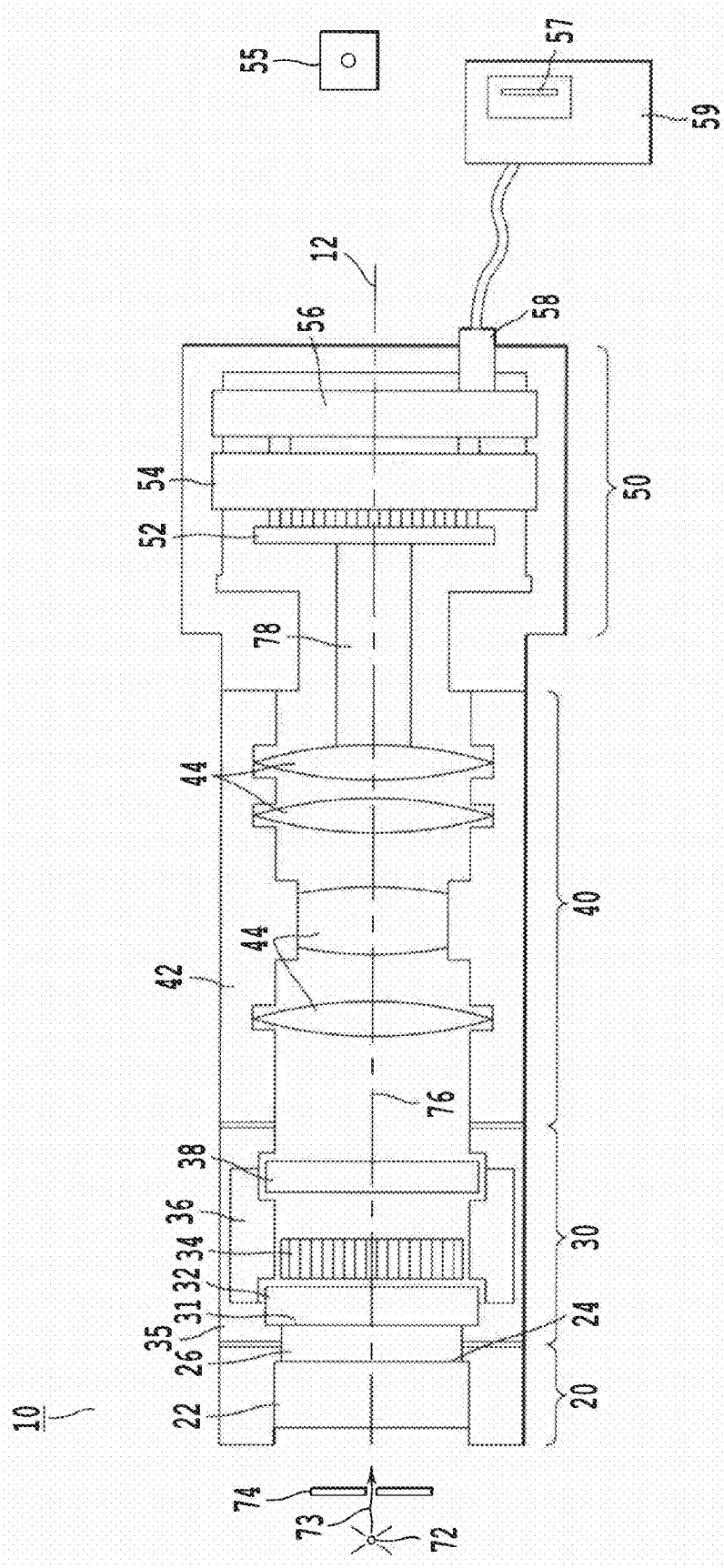
FIG. 2 shows a diagrammatical cross-sectional view of the gamma camera.

With respect to FIG. 2, a cross-sectional schematic view of a gamma camera 10 is shown. Along a propagation path or optical axis 12, the scintillator 20 arranged in the front end is used to absorb gamma rays or X rays from an emitting source 72 and can convert the absorbed rays into wavelengths readable by optical sensors, such as CCD or CMOS image sensors. In the variant shown, source 72 is a mouse that was injected with a tumor-seeking radioactive tracer. In the remaining portions of the description we will refer to gamma rays, but X rays can also be detected and processed by the gamma camera 10, and an X-ray camera is therefore a variant of the present invention. At a back surface 24 of the scintillator plate 22, a light emitting pattern is generated that produces light in the visible spectrum, produced by the crystals of the scintillator. The light emitting pattern typically produces light in the wavelengths between 300 nm and 1000 nm. The gamma rays may exit from a pinhole 73 of an aperture plate 74. An aperture plate 74 having multiple pinholes producing overlapping images can also be used. Plate 74 is arranged between scintillator 20 and gamma-ray source 72 to form an image of the radioactive source distribution producing the gamma rays. By way of an example, pinhole 73 may have a diameter between 100 µm and 1000 µm in an aperture plate 74 having a thickness of 1 mm made of lead, in the case that high-energy gamma rays are used. In a variant, the aperture plate 74 may be made of a thin sheet of platinum have a thickness between 25 µm and 50 µm sufficient to block low-energy gamma-rays (30 keV). Small pinholes provide a large field of view because of the small thickness of the platinum, and they can be used to provide high resolution imaging with high gamma-ray collection efficiency.

The scintillator 20 can be a columnar or structured scintillator, a polycrystalline screen of the type used in X-ray detectors, or a monolithic single crystal. A scintillation screen can also be used. The scintillator can also be made of elements of segmented crystals. Many different materials can be used for manufacturing the scintillator, the non-exclusive list includes columnar cesium iodide (Thallium) CsI(Tl), CsI(Na), NaI(Tl), $LaBr_3(Ce)$, gadolinium oxysulfide ($Gd_2O_2S$), also known as Gadox. The scintillator absorbs the rays at a certain interaction depth. A scintillation event has a duration of about 100 ns to 1 µs, depending on plate 22. In case gamma rays of higher energies have to be detected, the thickness of the scintillator plate 22 in a direction to the propagation path 12 is chosen relative thick. For example, the CsI(Tl) columnar scintillators preferably have a thickness between 100 µm and 3 mm, depending on the gamma-ray energy. More preferably, for such columnar scintillator the thickness is in a range between 2 mm and 3 mm for energies 140 keV photons from $^{99m}Tc$. In the case $Gd_2O_2S$ scintillators are used, they preferably have a thickness between 50 µm and 100 µm. Other types of scintillators can also be used that can convert rays of a photon energy of a range of 20 keV to 1 MeV into optical radiation, such as visible light. Other types of rays can be converted to photons, such as α and β rays. With such plate thicknesses, gamma-ray energies of up to several hundred keV can be detected. For example, it is possible to use energies of 511 keV that are available from the isotope fluorine-18. Further improvements in scintillator material technology and manufacturing techniques will allow the production of even thicker scintillator plates 22 that could be used for detectors that could absorb even higher gamma-ray energies.

After the scintillator 20, an optical coupler 26 and an image intensifier 30 are arranged so that the scintillator image generated on back surface 24 of plate 22 can be guided by an optical coupler 26 to enter a front surface 31 of the image intensifier 30. The optical coupler can be a fiber optic taper that can have a magnification or a minification ratio. In such configuration, rear surface 24 of plate 22 is in direct contact with the front surface of the fiber optical taper, and a back surface of the taper can be in direct contact with the front surface 31 of light intensifier 30. In an alternative, optical coupler 26 is made of a fiber-optic faceplate or a thin window.

For example, the optical coupler 26 can also be a lens with a high numerical aperture NA, in the range of 0.5 to 1.

In another variant, the back surface 24 of the scintillator plate 22 and the front surface 31 of the image intensifier 30 are directly coupled to each other without the use of optical coupler 26. The main goal of the optical interface between the scintillator 20 and the image intensifier 30, that is formed by either coupler 26, direct contact, high-efficiency lens coupling, or a combination thereof, is to minimize the light loss of the light emitted from the back surface 24 of the scintillator before entering intensifier 30. The configuration where the light exiting the scintillator 20 is immediately amplified by a light intensifier 30 is an important feature of the invention, because it provides a strongly amplified light or optical radiation from the scintillation event, that allows accurate estimation of a horizontal position, a vertical position, and a depth of interaction, and photon energy of the interaction of gamma ray source, based on the light emitting pattern captured as a cluster. In addition, it allows for the use of an inexpensive CCD/CMOS detector to capture scintillation events capable of running at rapid frame rates.

The scintillator image is amplified with image intensifier 30 by a luminous gain in a range between $10^4$ and $10^7$. The image intensifier includes a photocathode 32 at the light entrance side, having a front surface 31, made, for example, of at least one of Bialkali Antimonide, Multialkali Antimonide (for example S20), Multialkali Antimonide (for example S25), Gallium-Arsenic-Phosphorus (GaAsP), or Gallium Arsenide (GaAs), depending on the required luminous gain, resolution, and spectral matching requirements of the photocathode 32 and the scintillator 20. Other types of image intensifiers can also be used. After the photocathode 32, a micro-channel plate 34 (MCP) is arranged. In a variant, dual or multi-stack MCPs may be used to further intensify the luminous gain. For example, it is possible that a two-stage or two-stack image intensifier 30 is used, having two MCPs in series to add additional amplification. A fluorescent screen 38 at the exit of the image intensifier 30 produces an amplified, fluorescent image 76. A high voltage source 36 provides for the required electrical fields for the image intensifier 30. The rear face of image intensifier 30 can be configured for interconnection to standard optical lenses, such as C-mount, CS-mount, F-mount, K-mount lenses, etc. with various focal lengths. An exemplary image intensifier 30 that can be used is a military surplus AN/PVS-4 image intensifier having a single stage micro-channel plate, having 25 mm input and output active diameters, an S25 photocathode, and a fluorescent screen 38 made of P-43 phosphor.

After intensifier 30, the amplified image enters optical system 40 that is connected to intensifier 30. The optical system 40 can be made of multiple lenses 44 in a casing 42 that can magnify or minify the amplified image to project a measurement image onto an image sensor 52 of detector 50. The strong optical gain from the image intensifier 30 allows a flexible and customizable optical system 40 for various application requirements. For example, the optical system 40 can be freely chosen for the particular application, and due to large optical gain by intensifier 30, it is not necessary to use an optical coupling with very low light loss and/or low distortion. For example, a special configuration having different magnification or minification of the optical system 40 of the amplified image may be required. As an example, a first 50 mm lens and a second 400 mm lens from the manufacturer Nikon is used that are mounted in series, having a magnification of 1:8 so that small, inexpensive CMOS image sensors can be used. As another example, two 50 mm F/1.2 Nikkor lenses can be mounted face-to-face that can provide for a 1:1 magnification.

The optical detector 50 is arranged such that the focal plane of the image exiting the optical system 40 is projected on an image sensor 52 of the detector 50. After the scintillation event with the light emitting pattern is amplified via the image intensifier 30, a reduction of image intensity by the optical system 40 results, but the remaining image impinging on image sensor 52 is still strong enough that the noise and light loss of optical system 40 will not substantially affect the image capturing process and the measurements on the captured image. Therefore the image sensor 52 used by detector 50 need not to be very light sensitive. Standard CCD imaging sensors will be sufficient to generate an image that can be used for various measurements. Other types of solid state imagers such as CMOS imagers, thin-film imagers, etc. can also be used. In addition, with the gamma camera 10, no cooling of the image sensor 52 is needed that would substantially increase the costs of camera 10.

The image sensor 52 of detector 50 is coupled to driver unit 54 that is configured to read out the images that are captured by the image sensor 52. For example, all the CCD drivers, clock signal generators, supply and reference voltage generators, analog-to-digital converters, timing signal generators, memory buffers, etc. can be part of the driver unit 54. Driver unit 54 itself can be coupled to a processing unit 56 that can perform data and image processing on the images that are captured by the image sensor 52. The processing unit 56 includes a processor and memory that is configured to store computer-readable instructions that are able to perform various data processing, visualization and communication functions, when the instructions are executed on a processor. The memory can be volatile or FLASH memory, or a combination thereof. In addition, processing unit 56 may also include hardware-coded image processing chips, field-programmable gate arrays (FPGA), or complex programmable logic devices (CPLD) that can perform data processing such as image processing, feature extraction, statistical algorithms, and calibration algorithms, etc. For example, unit 56 may perform image filtering such as median filtering, image calibration, background image sensor noise calibration, statistical image analysis, center-of-gravity calculations, estimation, look-up table generation and management, etc.

In addition, the detector 50 may include an interface 58 that can communicate with an external device 59 or deliver images for visualization to an external screen. For example, raw image data or pre-processed image data can be transmitted to a personal computer or a specialized graphics computer for further processing, calibration, visualization, storage, and archiving. External device 59 may include a data reader 57, for example a Universal Serial Bus interface or a CD-ROM drive, and a computer-readable medium 55, for example a CD-ROM, DVD-ROM, USB flash drive, floppy disk, etc. can be read, written and erased by data reader 57, and a program stored on the medium 55 having computer-readable instructions can be transferred and executed on external device or unit 56.

Tests have shown the surprising results that by applying a strong optical gain at the beginning of the camera 10 just after the conversion of gamma-rays into light, instead of applying a substantial charge gain by using sophisticated image sensors 52 in the last stage of camera 10, the system is much less limited by light loss and allows great flexibility in the design of camera 10. Because of the strong luminous amplification by the image intensifier 30 of camera 10, and the efficient optical coupling of the scintillator 20 to the image intensifier 30, the light losses of the optical system 40 and the detector 50 are no longer significant comparing to the resulting intensified image. Therefore the design emphasis of the image sensor 52 can be put on relatively low-cost sensors that allows a high read-out speed, instead of having to use low-noise and highly sensitivity imagers, that may also require additional cooling, which can be very expensive.

In the variant shown, a Point Grey Research™ Flea 2 was used, having a resolution of 696×516 pixels, with 9.3 μm square pixels to facilitate measurements and capable of operation at 200 fps or 350 fps with 2×2 binning. In another variant, a SBIG Inc. STL-1001E camera was used having a KODAK™ image sensor KAF-1001E CCD with 1 k to 1 k pixels, and with square pixels with a size of 24.6 μm. Of course other image sensors of different technologies may be used, with other pixel sizes, pixel technologies and resolutions.

This combination of the use of the light intensifiers and low-cost detection units has lead to surprising and unexpected results allowing wide range of applications for different radiation energies. For example, the gamma camera 10 according to the invention leads to a substantial reduction of costs for detector 50 and image sensor 52 that are used to capture and measure scintillator events on the plate 22. In addition, lower-cost optical systems 40 can be used to couple the output screen 38 of the image intensifier 30 to a detector 50, allowing further cost reduction. Test results with a gamma camera 10 show that an intrinsic resolution to detect pinholes on plate 74 by the detector 50 is approximately 70 μm, an unexpected result in light of the available background art systems that use high-speed and low-noise imaging detectors. By choosing a different pinhole magnification, the resolution of gamma-ray projection images can be increased. The high-intrinsic resolution of the detector allows camera 10 to function as a gamma-ray microscope with the use of micro-coded apertures. Planar reconstructions have been achieved yielding an estimated reconstruction resolution to approximately 30 μm. In addition, the camera 10 is also designed to operate over a wide range of gamma-ray energies based on the scintillator plate thickness and light amplification. It has been demonstrated that the gamma camera 10 is capable of measuring radiation from isotopes used in small animal SPECT such as 125I having approximately 30 keV gamma-rays, 99 mTc with 140 keV gamma-rays, and 111In with both low energy X-rays (24-26 keV) and high energy gamma-rays (171 and 245 keV), and such results were unexpected in light of the existing solutions.

Moreover, gamma camera 10 according to the present invention also proposes an attractive, inexpensive modular design for the camera that can be used for high-resolution, multiple-pinhole applications such as molecular imaging and nuclear imaging, and the potential to be used as detectors in clinical SPECT imagers. Another advantage of the configuration of camera 10 is the ability to use ultra high-speed cameras with less sensitivity. The use of high frame rates permits the detection of high flux of gamma-rays without overlap of the clusters of pixels that are associated with different gamma rays. Thereby more information can be gathered and the detection resolution, precision and sampling frequency can be improved. The proposed gamma camera 10 has therefore a much higher count-rate capability for photons than cameras based on EMCCD sensor.

An additional aspect of the present invention is the processing unit 56, and the methods of processing the image data that is captured by the gamma camera 10 that can be performed by such processing unit 56. As discussed above, the methods of processing the image data can also be performed on external device such as a processing system 59, such as a personal computer, a parallel supercomputing processing system, dedicated graphics processing system, etc., or the processing unit 56 can also be a separate unit located outside of camera 10, but in communication with the camera 10. Special estimation techniques and combined with data processing algorithms that can be performed in real time can be implemented.

The gamma camera 10 is particularly suited for high energies of gamma-ray sources, because thicker scintillator plates 22 can be used, that absorb much higher energies, but also blurring of the light emitting pattern on the back surface 24 of plate 22 can be caused, thereby reducing a detector resolution depending on the depth of interaction. However, by the use of special estimation and processing algorithms with camera 10, it is possible to precisely calculate an effective horizontal position, a vertical position, and an energy of interaction of a gamma-ray inside a scintillator plate 22, as well as the depth of interaction (DOI) based on a light emitting pattern captured as image data in form of a cluster. By calculating or estimating the DOI, these effects of scintillator plate 22 can be compensated for.

Figure 3:
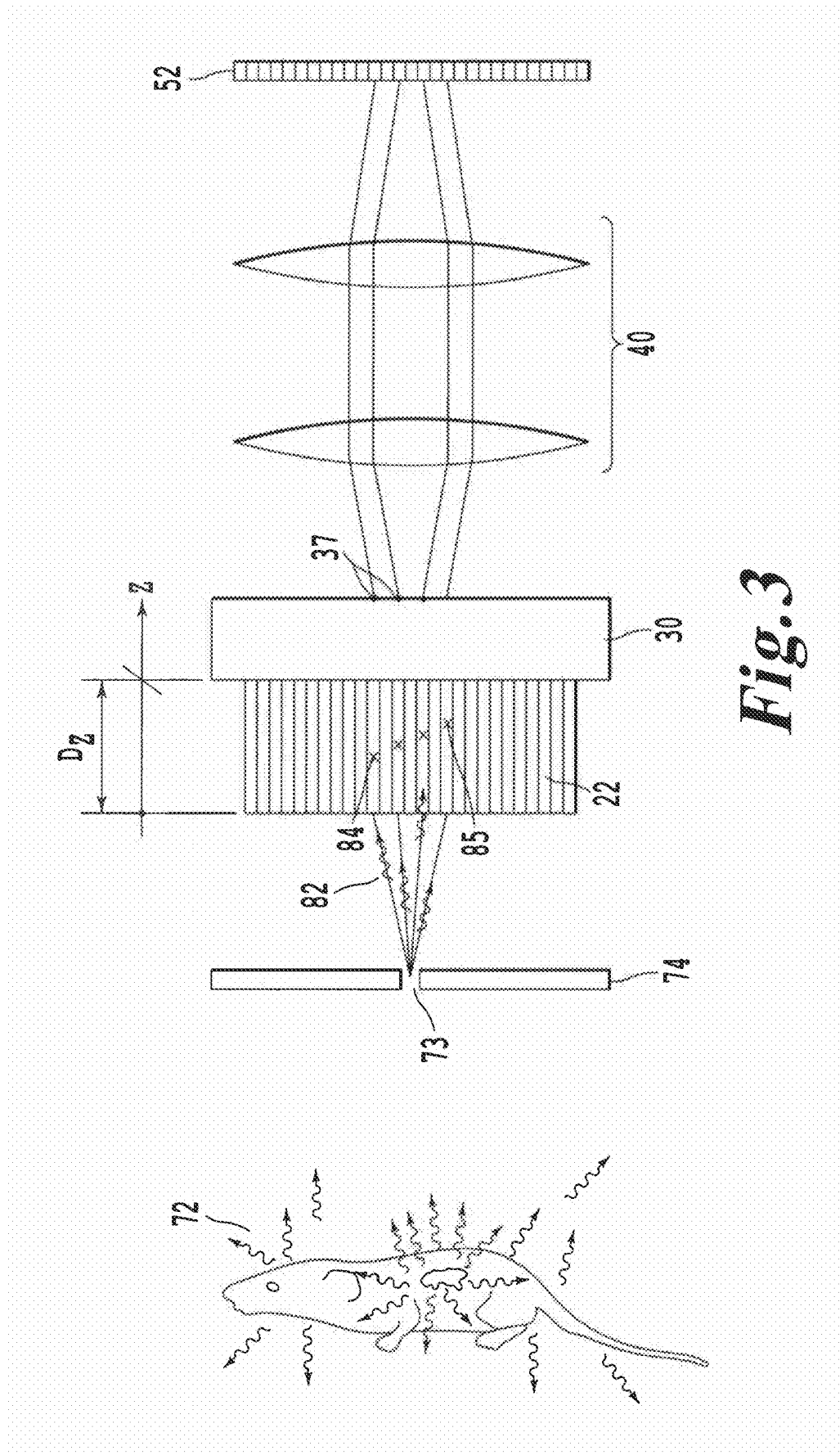
FIG. 3 shows a schematic cross-sectional view of a gamma camera depicting the depth of interaction of gamma-rays.

For example, as illustrated in FIG. 3, gamma-rays pass through a pinhole 73 of a plate 74 after being emitted by source 72, the rays may not progress perpendicularly from the aperture plate 74, but progress from pinhole 73 in different directions. These rays will impact and interact with the scintillator plate 22. In addition, the depth D, of the scintillator material allows that the rays will be absorbed at different depths 84, 85, mostly depending on the energy intensity of the gamma-ray, but also depending on the impact angle, and the material impurities and inconsistencies of plate 22. This penetration depth of the rays is called the Z-axis position or depth of interaction (DOI) of the gamma-rays.

The scintillator 22 can be considered to be made of homogeneous material with an attenuation coefficient μ which depends on the photon energy and the material. A fraction $1-(1/e)$ of the gamma photons, where e is equal to 2.718, are absorbed in a distance of $1/\mu$. At normal incidence, this distance is also approximately the range of the depths of interaction, but at oblique incidence the range of DOI is less than the absorption distance. DOI effects are observed in the clusters of imaging data from the image sensor 52 showing variability in the light intensity of the captured image, spatial variance, and kurtosis (peakedness), and other features, based upon gamma-ray DOI within the crystals of the scintillator plate 22.

In the case a columnar scintillator is used, scintillation light is partially guided towards the rear surface 24 of the scintillator plate 22, the light output varies as a function of the interaction depth. In other types of scintillators, for example scintillation screens made of Gadox and other X-ray phosphors, the light is scattered rather than guided, and for monolithic single crystals there is light spread during propagation from depth of interaction to the intensifier 30. For example, ray 85 that is absorbed at a deeper location than ray 84 will produce a brighter and less blurred light emitting pattern 37 on the back surface of the scintillator plate 22. The combined effect of the variable interaction depth and variable angle of impact of the gamma rays exiting from a pinhole 73 will produce such light emitting pattern 37 on the back surface 24 of the scintillator 20. Information of the light emitting pattern 37 that is projected onto the intensifier 30 can be subjected to calculation and estimation techniques to estimate the DOI, after capturing by sensor 52 as a cluster.

Accordingly, by using captured image data information from sensor 52 where a cluster represents a light emitting pattern 37, a four-dimensional parameter set including the effective horizontal position, vertical position, depth, and energy of an interaction of a gamma-ray can be calculated. This data can be represented by four different values as a interaction parameter set including X, Y, Z and E. However, it is also possible to first calculate features from the raw image data of the clusters, and then calculate the interaction parameter set from these features. For example, the raw image data of the clusters can be reduced to features such as a sum of all pixel amplitudes of pixels forming the cluster, spatial variance, location of the cluster, kurtosis representing how "peaked" a cluster is, etc. Moreover, the precision of the calculation of the interaction parameter set can be improved by using advanced statistical estimation methods, such as the use of a maximum likelihood estimation technique to estimate the parameter set from either the raw image data of the clusters, the features of the cluster, or both. The following description with respect to FIGS. 4A, 4B, 4C, 4D, 5, and 6, includes information related to the captured image data of detector 50 including clusters 92 representing light emitting patterns 37 and their relationship to the interaction parameter set.

Figure 4D:
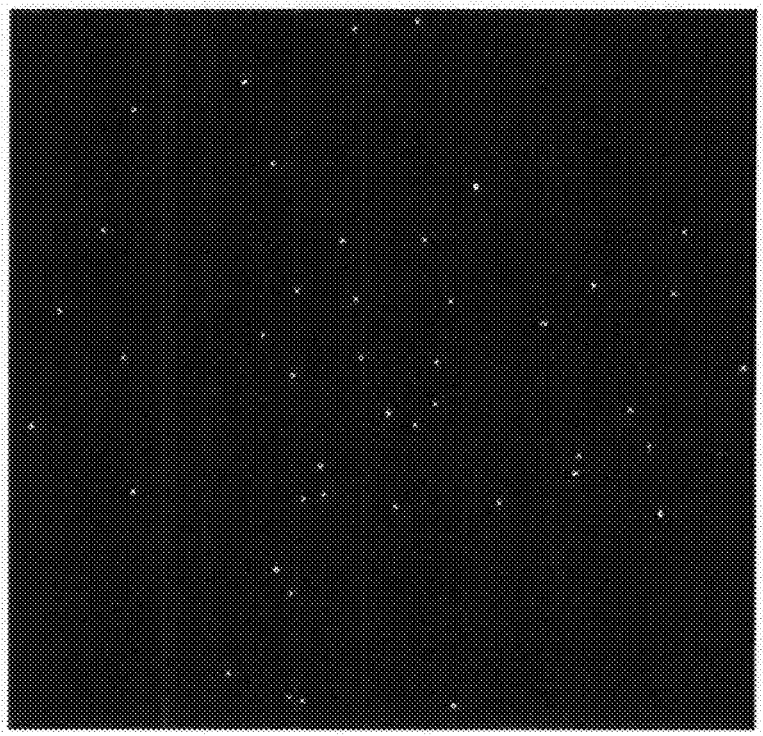
Figure 4C:
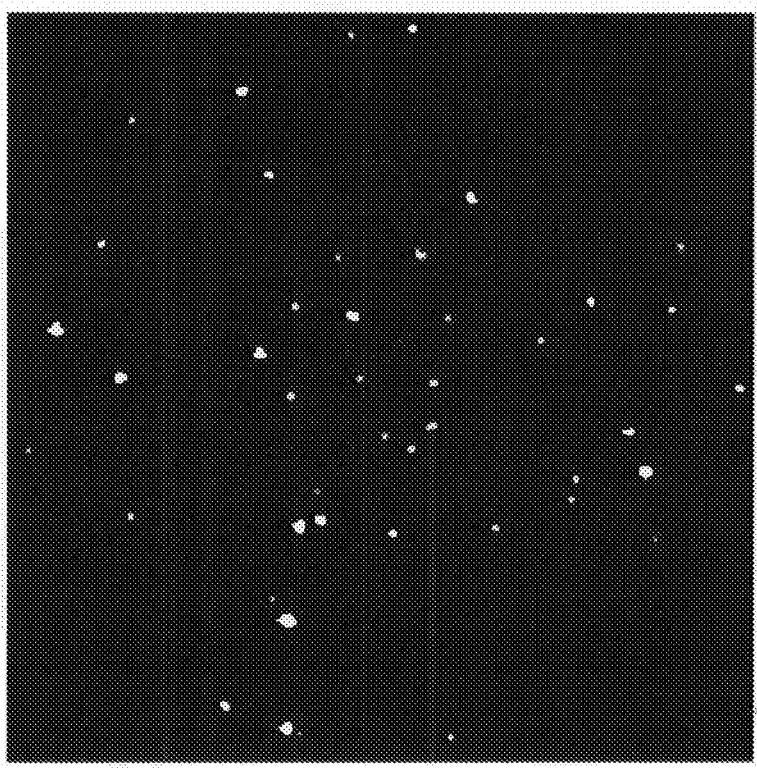

FIG. 4A represents an unprocessed captured image of the gamma camera and FIGS. 4B, 4C and 4D represent a series of processed image of the camera after performing image processing such as filtering by the processing unit 56. When gamma camera 10 captures images from rear face 24 of plate 22, the captured image 96 includes a series of clusters 92 and noise that is scattered throughout the unprocessed image 90. In order to improve the precision of the calculated or estimated interaction parameter set X, Y, Z, and E, the unprocessed image 90 can be subjected to various steps of filtering to obtain a processed image 96, thereby substantially removing the noise 93. Continuous regions of pixels form clusters 92 that represent gamma-ray interactions, and these cluster includes information that can be processed to extract an interaction parameter set X, Y, Z, and E for a particular interaction event. Several of such clusters 92 are shown in FIG. 4A, each representing a gamma-ray that traversed a pinhole and absorbed by plate 22. First, the unprocessed image 90 can be subjected to a noise removal filter, for example a median filter resulting in a filtered image shown in FIG. 4B. Other filter algorithms can also be used, such as low-pass filters, fixed pattern noise removal filters eliminating noise introduced by image sensor 52 of detector 50, calibration algorithms compensating optical distortions from the optical system 40 and intensifier 30, etc. Next, the image of FIG. 4B can be subjected to clipping with a thresholding algorithm to generate a processed image 96, and a component labeling algorithm may identify the clusters, as shown in FIG. 4C. Based on the processed image 96, the parameter set X, Y, Z, and E can be calculated or estimated in a next step, where the location of the interaction in X and Y direction is obtained as shown in FIG. 4D. Each calculated or estimated interaction position is shown in its X-Y position with a small dot.

Figure 5:
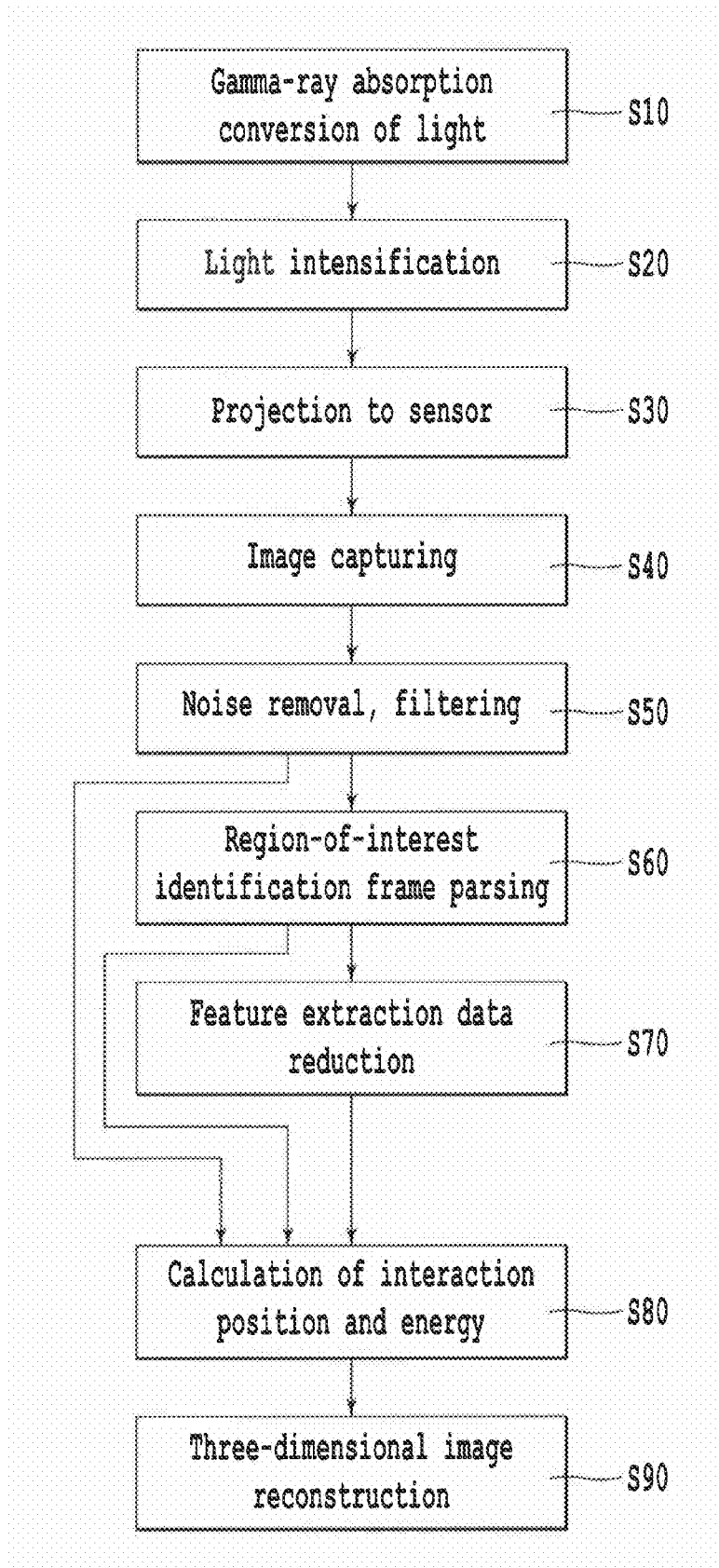
FIG. 5 shows a diagram representing the steps of a method to calculate or estimate interaction positions and the energy of a gamma ray according to another aspect of the present invention.

FIG. 5 depicts an exemplary diagram showing a method of calculating or estimating the interaction parameter set X, Y, Z, and E, according to another aspect of the present invention. In a first step S10, a gamma-ray interacts in the scintillator plate 22 and produces a light emitting pattern 37 on the back surface 24. Next, in step S20 the pattern 37 is directly amplified or intensified by intensifier 30. In step S30, the intensified light is projected to an active surface of image sensor 52 by an optical coupling system such as a lens, and the image is then captured by the image sensor 52 and converted to digital image data in step S40 for further processing. In a first pre-processing step S50, the digital image data is subjected to filtering and noise removal as described with reference to FIGS. 4A and 4B. Other pre-processing steps can be performed, such as compensation of distortions. Thereafter, in optional step S60 regions of interest (ROI) are identified that include clusters 92 representing light emitting patterns 37, as explained with respect to FIG. 4C. This step is also referred to as frame-parsing. It is also possible that first the ROI are identified with clusters 92 with step S60, and then the filtering step S50 is performed, depending on the quality of the unprocessed captured image. In case the captured image has too many clusters, and therefore identification of ROI would not be beneficial, it is possible to perform full frame processing to directly proceed to step S80.

To identify such ROI of the images captured by detector 50, a search algorithm can be implemented by processing unit 56 that searches the captured image and detects ROIs that include clusters 92, to avoid that data of an entire image frame is subjected to such calculations or estimations. In an example of such search algorithm, first a step including a coarse search can be performed over the entire image in a grid of reduced resolution, by using a log-likelihood algorithm to detect presence or absence of a cluster 92. In another step, locations having the highest likelihood above a certain threshold are selected, and a new local search can be performed with a higher resolution to find the exact positions of the clusters. In another step, based on the location information, a ROI can be defined that will include the cluster 92. Preferably, ROIs with a size ranging from 3×3 to 15×15 pixels can be further processed, allowing a substantial increase in processing speed comparing to an implementation where the entire image is processed. Of course other types of searches or detection algorithms can also be performed to detect the clusters 92 of an image.

It is also possible to use an image sensor 52 that allows the read-out of only a partial frame or a plurality of partial frames, without having to read out the entire image having a full resolution. Such image sensor readout method could be combined with the search methods to detect the cluster location. Once the location of a cluster is detected by a coarse search, for example by using the sub-sampling or pixel binning capabilities of a sensor, partial images including clusters could therefore be read-out at a substantial increased speed, by using the windowing function of the sensor. In an example, the reading out of four ROIs with a pixel area of 32 to 32 pixels from an image sensor with 1024 to 1024 resolution results in a potential speed-up of the read-out process by a factor 256.

In a next optional step S70, the raw image data of the ROIs including the clusters can be reduced by being subjected to feature extraction algorithms, where different features of a cluster 92 may be extracted. The features may include calculation of the sum of all pixels in the cluster, the centroid of clusters, spatial variance, kurtosis, circle-symmetry of a cluster, etc. These features can be calculated from each captured image, and need not to be based on statistical properties. For example, in step S70, it could be possible to implement an algorithm to eliminate two gamma-ray interaction events that occurred in close proximity to each other, thereby producing overlapping clusters, that would be detected as a single cluster. By calculating a features that represents a degree of circular symmetry (eccentricity) of the cluster, overlapping multiple clusters could be eliminated, because a single cluster would have a higher degree of circular-symmetry.

In step S80, the parameter set including the position and the energy of a gamma ray interaction is calculated, for example by using the sum of pixels to calculate the energy of the interaction, and the location of the centroids to calculate the interaction position. It is also possible to use a maximum-likelihood estimation using 2D spatial Gaussians fits to find the X, Y interaction location. Moreover, special techniques to estimate the parameters can be used, as further described below. These parameters representing the interaction position and energy can either directly be calculated from the image data from the ROIs of step S60, or from the image features of the optional step S70, thereby using a reduced data set. Other factors that may influence the calculation of the parameter set may be the configuration and hardware parameters of the image sensor 52. The parameters of the image sensor can be pixel delay time constants, integration time, frame rate, shuttering methods, etc. In step S90, further processing can be applied to the parameter set, such as calculation of visualization data with three-dimensional graphics processing, storage, analysis, data communication, etc.

An example of processing that can be performed in step S50 is a removal of distortions introduced by intensifier 30. Intensifier 30 can introduce artifacts to an intensified image. While some of these can be compensated for, others can be used as parameters to design the camera 10 and the operation conditions. Artifacts that may be introduced are lag, vignetting effects, pincushion distortion, and the S distortion, depending on what type of intensifier 30 is used. The lag of an intensifier 30 is the persistence of luminescence that acts like a low-pass filter on the light emitted from back face of intensifier 30, and can be expressed as a time constant. This time constant may limit the precision of the calculation of the interaction position and energy, and can also limit the frame rate that is usable. The time constant may also increase with the lifetime of the camera 10. Vignetting is an effect that causes a fall-off in brightness at the periphery of an intensified image, is caused by the concentrated collection of light at the center of the image intensifier 30 around the optical axis 12 compared with the light at a periphery. Therefore it is possible that intensifier 30 has a better resolution, increased brightness, and less distortion around the optical axis.

The intensifier 30 may also cause geometric distortions such as the pincushion distortion and the S distortion. Pincushion distortion is a geometric, nonlinear magnification across the image, where a magnification difference at the periphery of an intensified image and can be caused by intensifier 30 and the optical system 40. The S distortion of the intensified image is caused when electrons inside intensifier 30 move in paths along designated lines of flux. External electromagnetic sources affect electron paths at the perimeter of intensifier 30 more so than those nearer the optical axis 12. This characteristic causes the exiting intensified image to distort with an S shape. Intensifiers with larger diameters are more sensitive to the electromagnetic fields and thereby show increased S distortion. The processing unit 56 or external device 59 can be configured to store calibration data and algorithms to compensate for the artifacts that are introduced by intensifier 30, to further increase a detection precision of camera 10. In particular, the geometric distortions, and the distortions of image intensities such as the vignetting can be compensated.

Figure 6:
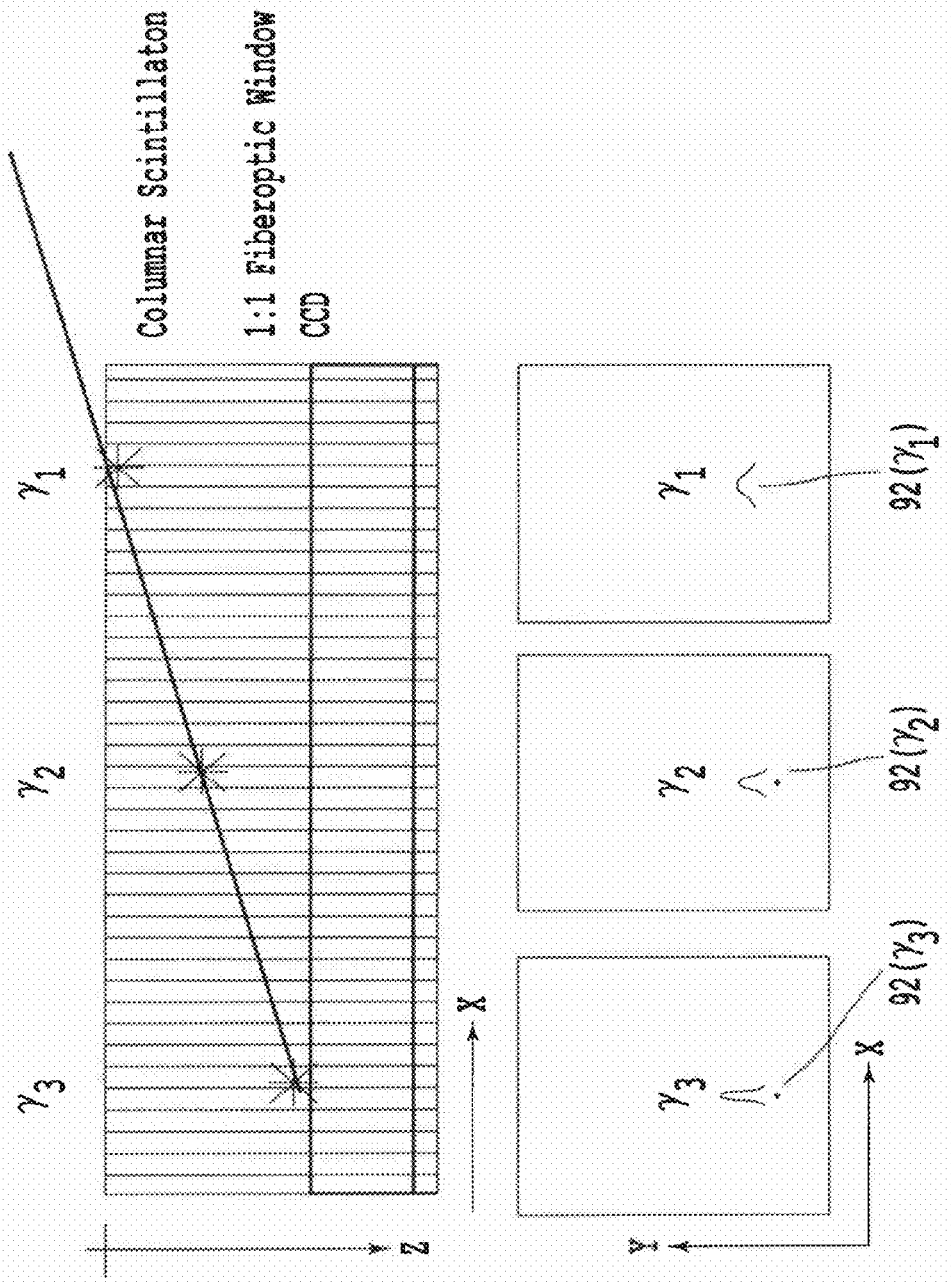
FIG. 6 shows graphs that represent different images that are produced by the gamma camera as a result of different depths of interaction.

Based on the optical information included in a cluster 92 that represents a light emitting pattern 37, processing unit 56 can estimate an interaction parameter set X, Y, Z, and E. Each cluster 92 corresponds to one interaction event at a certain time instant that is captured by a readout frame from image sensor 52. Such estimation techniques yield higher accuracy of the interaction parameters comparing with the use of a centroid and the sum of pixels to calculate the position and energy of the interaction. For further explanation FIG. 6 is presented showing more detail of the image clusters that can be generated by thee different gamma-rays $\gamma_1$, $\gamma_2$, and $\gamma_3$ of different energies. The Z-coordinate relates to the depth of interaction (DOI), and the Z-axis is parallel to an optical axis 12 of the gamma camera 10. The X and Y coordinates refer to a Cartesian coordinate system of the planar surface of the image sensor 52, representing a horizontal and a vertical position. It can be seen that the gamma-ray $\gamma_3$ that interacts at a deeper DOI in the columnar scintillator statistically produce a stronger light cluster signal with less variance of the pixels in X and Y direction, while the gamma-ray $\gamma_1$, that interacts at a shallower DOI in the scintillator produces a weaker light cluster signal of less light intensity, it also has more variance in an X and Y direction. The respective light intensity profiles for the clusters 92 ($\gamma_1$), 92 ($\gamma_2$) and 92 ($\gamma_3$) are also represented, and show the decreasing intensity and increasing variance with for decreasing DOI values. This information included in a cluster can be subjected to statistical analysis, to extract highly precise information to estimate parameter sets X, Y, Z, and E.

Therefore, according to another aspect of the present invention, the captured image data representing a cluster can be subjected to a maximum-likelihood estimation (MLE) algorithm that will produce an interaction parameter set X, Y, Z, and E for an effective interaction. This processing can be part of step S80. Although more processing is required comparing to a simple centroid calculation, the use of an MLE according to this aspect of the invention will provide increased resolution of the interaction parameter set X, Y, Z, and E. The result of the MLE estimation are the values of Z, Y, Z and E that maximize the probability of the data conditional on X, Y, Z and E for the observed data in each cluster. A likelihood function is a conditional probability of the data given a set of parameters, denoted generally as Prob(data | parameters), where the data are a set of experimental values and the parameters are the unknown quantities to be estimated. In our case, the data are either the pixel values in a captured cluster 92 or a set of features derived from the cluster 92. The unknown parameters are the X, Y, Z and E for the scintillation event that produced the cluster. Maximum-likelihood estimation then chooses the X, Y, Z and E that maximizes prob(data | X, Y, z, E) for the data values that are actually observed for the cluster.

The proposed MLE also needs calibration data, that can be stored and pre-processed by the processing unit 56 or external device 59. For this purpose, a series of calibration measurements with a calibration aperture sheet with several pinholes or with a collimated beam can be taken that will be used for the MLE algorithm. The calibration data can be made specific to every single camera and could take several inconsistencies into account from the entire optical path, such as missing pixels, optical distortions, inhomogenities of the light intensifier 30, etc. The calibration data could therefore incorporate information compensating optical distortions introduced by intensifier 30 and optical system 40, and therefore no other optical calibration algorithms would be required.

When generating calibration data for the MLE algorithm, a mean cluster template set can be generated for each depth of interaction in the plate 22, for a range of different gamma-ray intensity energies. In addition, multiple mean cluster templates can be generated for various X and Y positions of the interaction event in the plate 22. This may particularly be interesting to compensate for non-homogeneities in X and Y direction of different scintillator plates 22, and can be a camera-specific calibration. For the same energy, position, and depth of interaction, many samples of clusters can be stored and a mean cluster value can be generated. To generate such data, a set of features from image date from a cluster 92, including a sum of all pixels included in the cluster, spatial variance of the cluster, and kurtosis can be assigned by a table to a particular interaction parameter set X, Y, Z, and E for an effective interaction. The table can be stored in each camera 10 and can be used as a look-up table to speed up processing of data. Therefore, by calculating a set of features from cluster 92, it is possible to directly obtain the interaction parameters by the use of the look-up table.

Figure 7A:
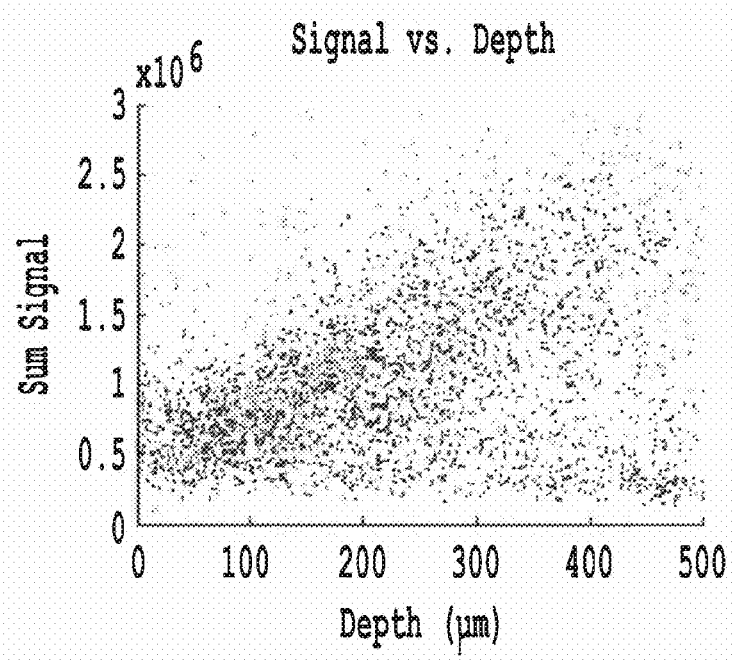
FIGS. 7A, 7B, 7C, 7D, and 7E represent graphs showing the dependence of the depth of interaction and different image features that can be extracted from clusters.
Figure 7B:
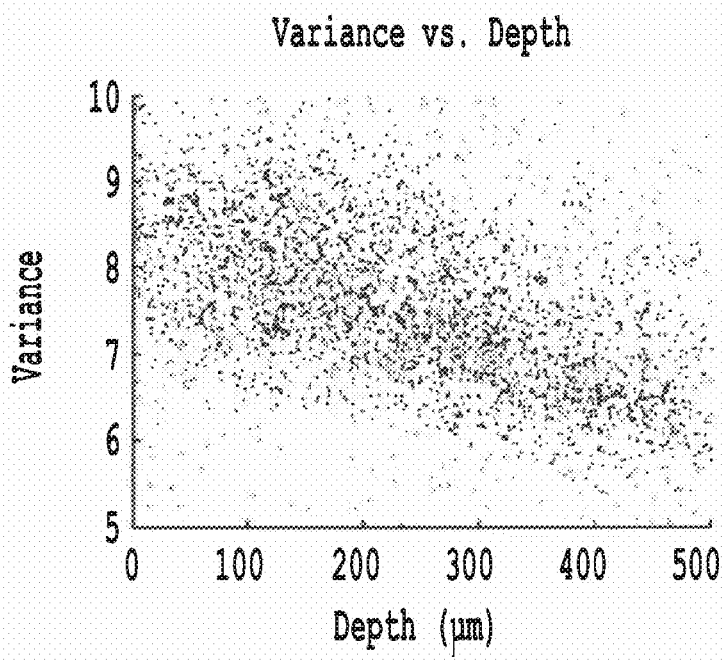

As an example for calibration data that can be used for the MLE, FIGS. 7A to 7B represent a series of measurements performed by the gamma camera 10 at different time instants with a beam formed by a collimated gamma ray source. In these measurements, clusters 92 were generated on a plate 22, and the clusters are captured by sensor 52 are represented as a sum signal and the cluster pixel variance that are spread out in X and Y direction is represented as a function of the DOI in plate 22. From FIG. 7A is can be seen that with increased DOI, the signal intensity statistically increases, but there is still a strong variance of different possible signal intensities. As shown in FIG. 7B the pixel variance of a cluster decreases linearly with increased DOI, but again there is a strong variance in the obtained measurements. The representations of FIGS. 7A and 7B further support the use of statistical algorithms based on calibration data that can improve the precision when calculating an interaction parameter set X, Y, Z, and E, to reduce the effects of data spread over time.

Figure 7C:
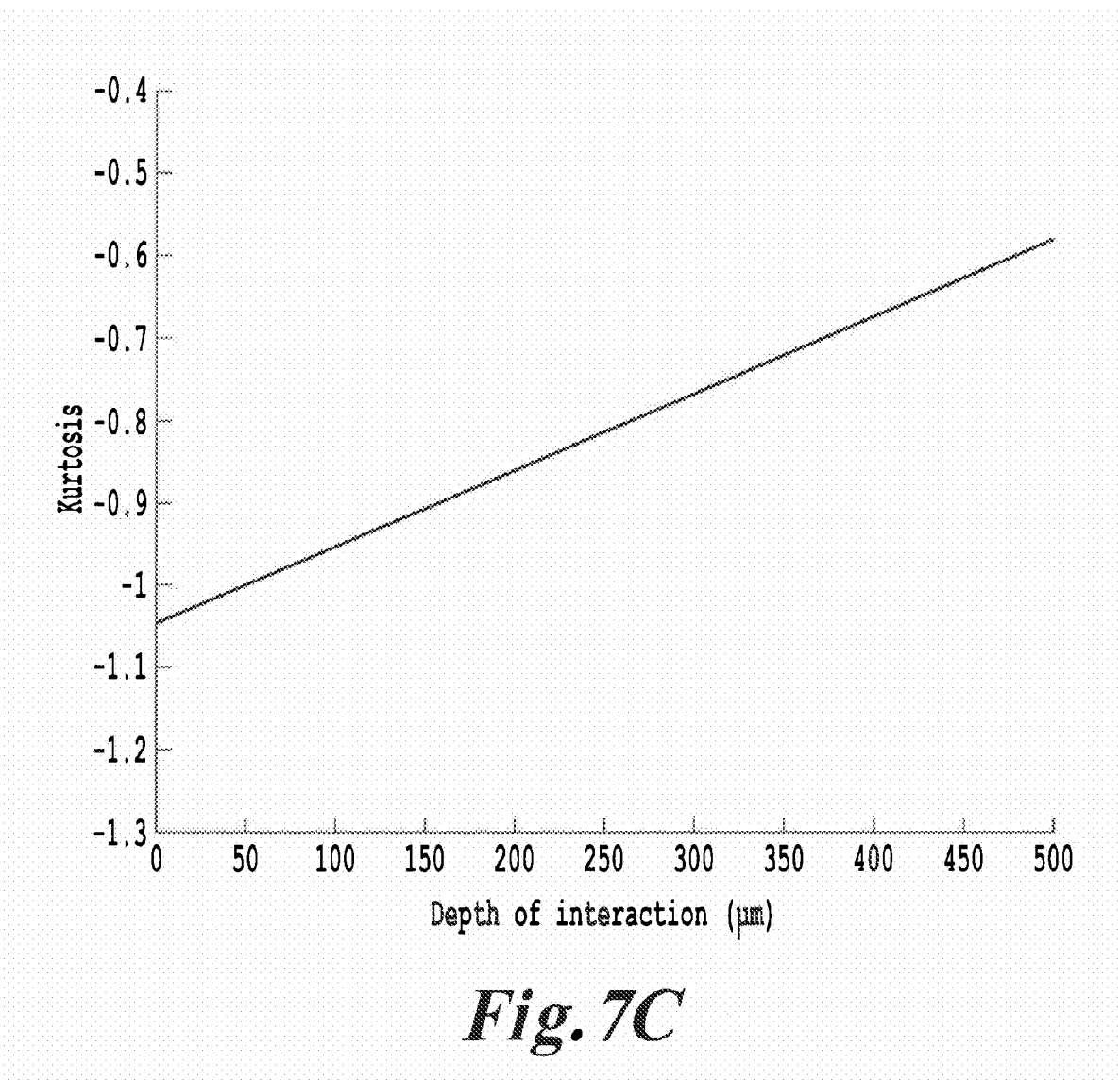
Figure 7D:
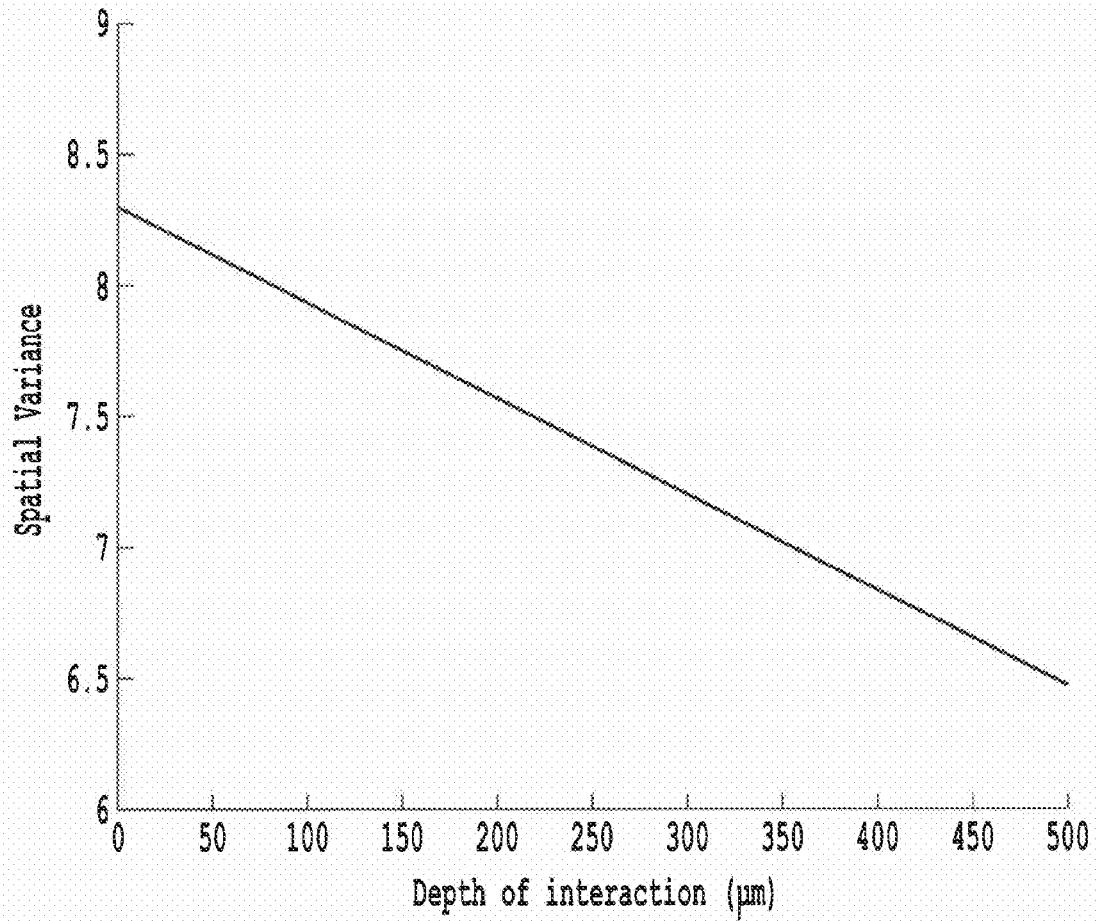
Figure 7E:
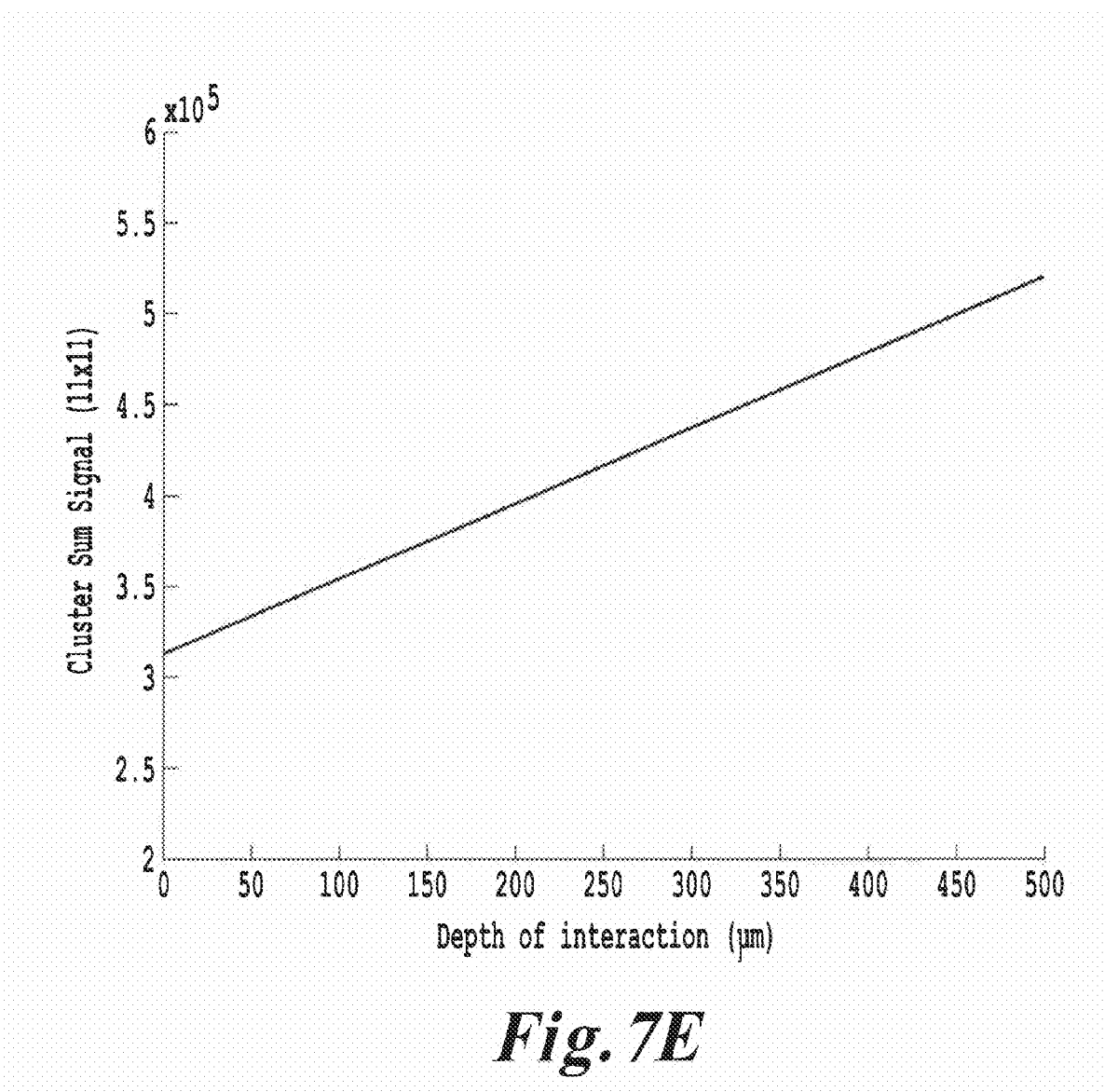

FIGS. 7C, 7D, and 7E schematically represent different features that can be extracted from the image data of a cluster 92. FIG. 7C represents the kurtosis of clusters, as a function of the depth of interaction in plate 22. With increased depth of interaction, the kurtosis value increases from about −1.05 to −0.6 linearly. FIG. 7D depicts the spatial variance of clusters 92 as a function of the spatial variance. Decreasing spatial variance signifies a deeper interaction depth. FIG. 7E shows the cluster sum signal as a function of the depth of interaction, showing an increasing sum signal for deeper interaction depths. In other words, if a gamma-ray interactions at a deeper depth closer to the rear surface 24 of scintillator plate 22, the clusters 92 appear brighter, but become statistically smaller in diameter.

FIG. 8 depicts a three-dimensional representation of a series of three-dimensional estimations of interaction positions of individual gamma rays forming a beam through the scintillator from a collimated gamma-ray source. The collimated beam was incident to the scintillator plate 22 at an angle, and therefore samples of various penetration depths within the crystal of the plate 22 are generated. The Z-axis represents a depth of interaction of the gamma-ray, and the X and Y axis represent the horizontal and vertical positions of the interaction on the plate 22. Because the angle of arrival of the collimated beam and the energy is known, a mean cluster template, dependent on depth of interaction within the scintillator, is generated from many interactions and serves as calibration data. Preferably, 10,000 to 100,000 gamma-ray interactions from the collimated beam are taken for calibration purposes, from the same energy level. Thereafter, a given cluster generated by a particular gamma-ray interaction is identified and the mean cluster template is used to find the maximum-likelihood thee-dimensional position and energy estimate for interaction.

The data processing of clusters 92 to extract the interaction parameter sets may require substantial processing power, especially if real-time processing for three-dimensional visualization is required. Such processing can be performed in the processing unit 56 or an external processing device 59. For example, steps S50 and S60 including the pre-processing with calibration, filtering and ROI detection can be performed in the processing unit 56, while steps S70, S80 and S90 requiring higher processing performance, including MLE and three-dimensional reconstruction can be performed in the external processing device 59. Memory of the processing unit 56 or external device 59 can be used to store extensive calibration data for a camera 10, and to create look-up tables that can increase the computing performance when performing an estimation.

Figure 9:
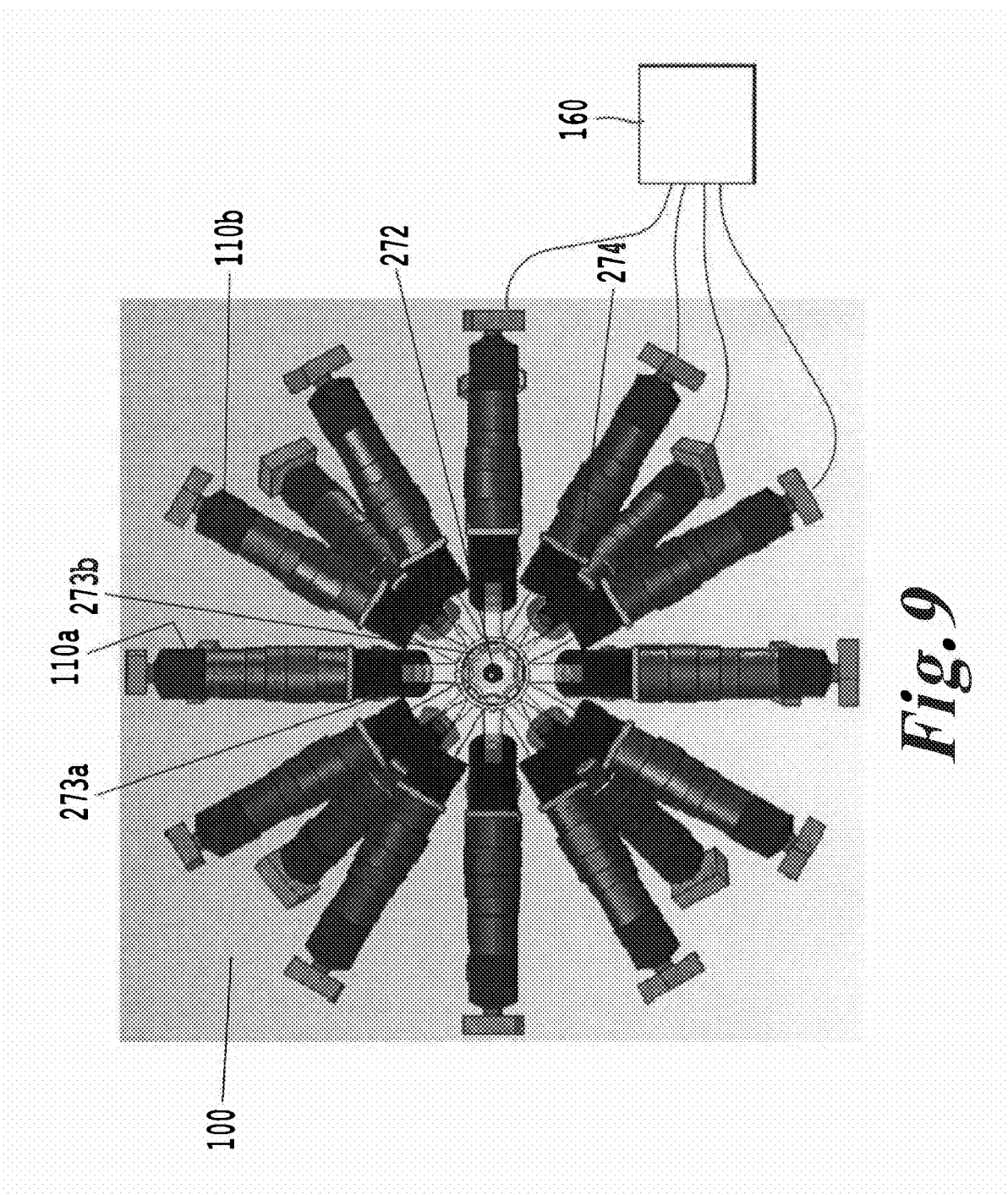
FIG. 9 shows a diagrammatical cross-sectional view of a system for capturing three-dimensional image data according to another aspect of the invention.

Another embodiment of the present invention is shown in FIG. 9, where multiple gamma cameras 110a, 110b, etc. are exposed to an inspection area 272 where a gamma-ray source is arranged, to form a system for capturing three dimensional imaging data that can be used for tomography. The inspection area is thereby viewed from different angles, which allows three-dimensional measurements from the inspection area. In the variant shown, a multitude of gamma cameras 110a, 110b, etc, are arranged concentrically around the inspection area, and the angles of the optical axes between each gamma camera are substantially the same. The optical axes of each camera 110a, 110b, etc. are arranged such that they intersect with the inspection area that is arranged in the center. For each gamma camera 110a, 110b, etc, a pinhole 273a, 273b is arranged with a respective aperture plate 274. The aperture plate 274 is arranged concentrically around the inspection area. A distance between a front surface of the gamma camera 110a, 110b and the corresponding aperture plate 274 is in a range between 2 mm to 200 mm. A processing unit 160 can be connected to the gamma cameras 110a, 110b, etc. and can process the image information that has been collected from all the gamma cameras, for example to perform three-dimensional imaging and displaying results thereof.

In another embodiment as shown in FIG. 10, a cross-sectional diagrammatic view of a gamma camera system 200 is provided, where a scintillator plate 222 having a large surface is inspected by multiple detectors 250a, 250b, 250c, in a tiling configuration. The rear surface 234 of the plate 222 can have a size of 15 cm to 15 cm, but even bigger plates for clinical purposes could be used. For purposes of clarity, only three detectors 250a, 250b, 250c are shown in a vertical direction, but any number of detectors are also possible, for example the same number of detectors in horizontal direction, thereby having a total of nine detectors inspecting one scintillator plate 222. The rear surface 224 of scintillator plate 222 has different areas or portions that can be inspected by multiple detectors 250a, 250b, 250c. In the configuration shown fiber optical tapers 226a, 226b, 226c are in direct contact with surface 224 and guide optical radiation from surface 224 to image intensifiers 230a, 230b, 230c, respectively. In another variant, other types of optical elements can be used instead of tapers 226a, 226b, 226c, for example lenses with prism assemblies, or lenslet arrays for the particular configuration of tiling. With such lenses or lenslet arrays, it is possible to have overlapping inspection areas of back surface 224, to avoid loss of information at an interface of two inspection areas.

The light intensifiers 230a, 230b, and 230c are connected to respective optical coupling systems, 240a, 240b, 240c, for example C-mount lenses. In turn, the optical coupling systems 240a, 240b, and 240c are connected to detectors 250a, 250b, 250c that can read the optic radiation emitted from the rear surface 224 of scintillator plate. The detectors 250a, 250b, 250c may be connected to a processing unit 260 that allows processing of the information gathered by detectors 250a, 250b, 250c, and can display results to a user.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

For example, throughout the description gamma rays have been described that are interacting with scintillator plates. However, the same principles can also apply and be used for X-rays that are absorbed by a scintillator plate made of a suitable material, for example CsI(TI) or higher-Z bismuth germanate (BGO). In addition, many other types of devices can be used for the image intensifier 30.

The invention claimed is:

1. A gamma-ray imaging device, comprising:
   a scintillator which converts gamma rays into localized flashes of light;
   an image intensifier that collects a substantial fraction of the light from each flash produced by a single gamma-ray photon and produces an amplified flash of light;
   an optical system including a video camera to image each amplified flash onto an imaging detector that operates at a frame rate fast enough to allow spatial separation of most of the clusters of pixels that receive light from different gamma-ray interactions in the scintillator; and
   a processing unit programmed with instructions, the instructions when executed identify the clusters of pixels on the video camera associated with respective amplified flashes of individual gamma-ray photons and use the data from said cluster of pixels to perform a statistical estimation of a position where the corresponding gamma-ray photon interacted with the scintillator and the energy deposited in the interaction.

2. The gamma-ray detection device according to claim 1, wherein optical radiation of each amplified flash has a wavelength in a range from 100 nm to 1000 nm.

3. The gamma-ray detection device according to claim 1, wherein the scintillator comprises at least one of a columnar scintillator, a scintillation screen, or a monolithic scintillator.

4. The gamma-ray detection device according to claim 1, wherein the optical intensifier comprises:
   a photocathode made of at least one of Bialkali Antimonide, Multialkali Antimonide, Gallium-Arsenic-Phosphorus (GaAsP), or Gallium Arsenic (GaAs).

5. The gamma-ray detection device according to claim 4, wherein the optical intensifier further comprises a microchannel plate.

6. The gamma-ray detection device according to claim 1, wherein said processing unit is configured to:
   subtract a background image from the interaction image associated with the light from the different gamma-ray interactions;
   identify pixels of the interaction image that are above a certain threshold intensity value within a region-of-interest to define a cluster;
   calculate a centroid of the cluster; and
   generate a mean value of all the pixel that are located within the region-of-interest.

7. The gamma-ray detection device according to claim 1, wherein said processing unit is configured to:
   use a maximum-likelihood algorithm to estimate a vertical position, a horizontal position, said energy, and a depth of interaction of the gamma-rays in the scintillator.

8. The gamma-ray detection device according to claim 1, wherein a rear surface of the scintillator and a faceplate of the image intensifier are in direct contact with each other.

9. A system for capturing tomographic imaging data comprising:
   a plurality of aperture plates arranged around an inspection area, the plates having at least one pinhole; and
   a plurality of gamma-ray detection devices according to claim 1 arranged around the inspection area so that a plurality of respective optical axes of the plurality of gamma-ray detection devices intersect with the inspection area, the plurality of aperture plates arranged between the detection devices and the inspection area,
   wherein each of the plurality of gamma-ray detection devices are arranged at a different angle of orientation towards the inspection area.

10. The system for capturing tomographic imaging data according to claim 9, wherein
   a distance from a front surface of the gamma-ray detection devices and the corresponding aperture plates is a range of 2 mm to 200 mm.

11. The gamma-ray detection device according to claim 1, wherein the intensifier comprises:
   a first image intensifier configured to intensify optical radiation from a first portion of a rear surface of the scintillator to generate first intensified optical radiation;
   a second image intensifier configured to intensify optical radiation from a second portion of the rear surface of the scintillator to generate second intensified optical radiation;
   a first and second optical coupling system configured to guide the first and second intensified optical radiation, respectively; and
   a first and second detector configured to detect the first and second intensified optical radiation and to generate first and second images, respectively, representing respective gamma-ray interactions in the scintillator.

12. The gamma-ray detection apparatus according to claim 11,
   wherein the first portion and the second portion of the rear surface of the scintillator are overlapping.

13. The gamma-ray detection apparatus according to claim 11, further comprising:
   a lens unit configured to split the optical radiation from the rear surface of the scintillator into optical radiation from a first portion and a second portion of the rear surface of the scintillator, respectively.

14. A method for gamma-ray imaging, comprising:
   in a scintillator, converting gamma rays into localized flashes of light;
   collecting a substantial fraction of the light from each flash produced by a single gamma-ray photon and producing an amplified flash of light with an image intensifier;
   imaging each amplified flash onto an imaging detector that operates at a frame rate fast enough to allow spatial separation of most of the clusters of pixels that receive light from different gamma-ray interactions in the scintillator; and
   identifying the clusters of pixels on the video camera associated with respective amplified flashes of individual gamma-ray photons and using the data from said cluster of pixels to perform a statistical estimation of a position where the corresponding gamma-ray photon interacted with the scintillator and the energy deposited in the interaction.

15. The method according to claim 10, wherein said identifying further comprises:
   filtering digital data of the imaged amplified flashes to remove noise by a median filter; and identifying the cluster of pixels by using a thresholding algorithm that is applied to the filtered digital image.

16. The method according to claim 14, wherein said identifying further comprises:

storing calibration data representing reference clusters generated from a plurality of interaction depths and gamma-ray energies; and comparing the cluster of pixels of the digital data image with the reference clusters by using a maximum-likelihood algorithm to estimate a horizontal position, a vertical position, a depth, and the energy of the interaction of the gamma-ray in the scintillator.

17. The method according to claim 14, wherein said method further comprises:

calculating a kurtosis value for the cluster of pixels, wherein said step of processing the digital data image subjects the kurtosis value to the maximum-likelihood estimation.

18. The method according to claim 14, wherein in said step of processing the digital data image by the maximum-likelihood estimation, the maximum-likelihood estimation uses calibration data based on an eccentricity of the cluster.

* * * * *